United States Patent
Chen et al.

(10) Patent No.: US 10,315,160 B2
(45) Date of Patent: Jun. 11, 2019

(54) INTEGRATED PURIFICATION METHOD AND SYSTEM FOR THE INDUSTRIAL EXHAUST GAS CONTAINING CYANIDES, HYDROCARBONS AND $NO_x$

(71) Applicant: BEIJING UNIVERSITY OF CHEMICAL TECHNOLOGY, Beijing (CN)

(72) Inventors: Biaohua Chen, Beijing (CN); Runduo Zhang, Beijing (CN); Jie Zhang, Beijing (CN); Dongjun Shi, Beijing (CN); Yingxia Li, Beijing (CN)

(73) Assignee: BEIJING UNIVERSITY OF CHEMICAL TECHNOLOGY, Beijing (CN)

( * ) Notice: Subject to any disclaimer, the term of this patent is extended or adjusted under 35 U.S.C. 154(b) by 0 days.

(21) Appl. No.: 15/568,461

(22) PCT Filed: Mar. 4, 2016

(86) PCT No.: PCT/CN2016/075602
§ 371 (c)(1),
(2) Date: Oct. 20, 2017

(87) PCT Pub. No.: WO2017/121022
PCT Pub. Date: Jul. 20, 2017

(65) Prior Publication Data
US 2018/0111084 A1    Apr. 26, 2018

(30) Foreign Application Priority Data
Jan. 12, 2016    (CN) .......................... 2016 1 0019224

(51) Int. Cl.
*B01D 53/72* (2006.01)
*B01D 53/78* (2006.01)
(Continued)

(52) U.S. Cl.
CPC ............. *B01D 53/72* (2013.01); *B01D 53/30* (2013.01); *B01D 53/56* (2013.01); *B01D 53/78* (2013.01);
(Continued)

(58) Field of Classification Search
CPC ........ C07C 255/08; Y02P 20/52; Y02P 20/51; B01D 53/8668; B01D 53/805;
(Continued)

(56) References Cited

U.S. PATENT DOCUMENTS 3,053,613 A * 9/1962 Andersen ........... B01D 53/8628
423/219
3,895,050 A * 7/1975 Sheely .................. C07C 255/00
546/286

(Continued)

FOREIGN PATENT DOCUMENTS

CN       1903415 A1    1/2007
CN     101362051 A1    2/2009
(Continued)

OTHER PUBLICATIONS

PCT International Search Report for PCT Application No. PCT/CN2016/075602 with full English translation, 8 pgs. (dated Oct. 9, 2016).
(Continued)

*Primary Examiner* — Timothy C Vanoy
(74) *Attorney, Agent, or Firm* — Womble Bond Dickinson (US) LLP (57) ABSTRACT

An integrated purification method and an integrated purification system for an industrial exhaust gas containing cyanides, hydrocarbons and $NO_x$. The method comprises the steps of: 1) subjecting the exhaust gas containing pollutants such as cyanides, hydrocarbons and nitrogen oxides ($NO_x$) to a gas-liquid separation device (1) to separate the free (Continued)

fluid, then mixing with the air blown by the air blower (201, 202), and preheating by the heating unit; 2) the mixture entering into the selective catalytic combustion (SCC) reactor (5) for the selective catalytic combustion reaction to convert harmful substances into $CO_2$, $H_2O$ and $N_2$, the catalysis being performed in two stages: the earlier stage is catalyzed by supported molecular sieve catalyst, and the latter stage is catalyzed by supported precious metal catalyst; and 3) the gas came out from the SCC reactor (5) entering into the heating unit to recover the heat, and then the purified exhaust gas being discharged directly through the chimney (6). The system comprises a gas-liquid separation device (1), a heating unit and a selective catalytic combustion reactor (5), a gas outlet of the gas-liquid separation device (1) being connected to the selective catalytic combustion reactor (5) through the heating unit, and an exhaust gas outlet of the selective catalytic combustion reactor (5) being connected to a chimney (6) through the heating unit.

9 Claims, 2 Drawing Sheets (51) Int. Cl.

| | | |
|---|---|---|
| *B01D 53/86* | (2006.01) | |
| *B01J 29/46* | (2006.01) | |
| *B01J 35/04* | (2006.01) | |
| *F23J 15/02* | (2006.01) | |
| *B01D 53/56* | (2006.01) | |
| *B01D 53/30* | (2006.01) | |
| *B01J 37/02* | (2006.01) | |
| *B01J 35/00* | (2006.01) | |
| *B01J 23/44* | (2006.01) | |
| *C07C 255/08* | (2006.01) | |

(52) U.S. Cl.
CPC ............ *B01D 53/86* (2013.01); *B01D 53/864* (2013.01); *B01D 53/865* (2013.01); *B01D 53/8621* (2013.01); *B01D 53/8625* (2013.01); *B01D 53/8628* (2013.01); *B01D 53/8668* (2013.01); *B01D 53/8696* (2013.01); *B01J 23/44* (2013.01); *B01J 29/46* (2013.01); *B01J 35/0006* (2013.01); *B01J 35/04* (2013.01); *B01J 37/0246* (2013.01); *F23J 15/02* (2013.01); *B01D 2255/1021* (2013.01); *B01D 2255/1023* (2013.01); *B01D 2255/20761* (2013.01); *B01D 2255/504* (2013.01); *B01D 2255/904* (2013.01); *B01D 2257/408* (2013.01); *B01D 2258/0283* (2013.01); *B01J 2229/66* (2013.01); *C07C 255/08* (2013.01); *F23J 2219/10* (2013.01)

(58) Field of Classification Search
CPC ................ B01D 53/8625; B01D 53/78; B01D 53/8621; B01D 53/8628; B01D 53/864; B01D 53/8696; B01D 2255/904; B01D 2257/408; B01D 2258/0283; B01D 53/56; B01D 53/72; B01D 53/86; F23J 15/02; B01J 2229/66
See application file for complete search history.

(56) References Cited

U.S. PATENT DOCUMENTS

| | | | | |
|---|---|---|---|---|
| 3,988,423 | A * | 10/1976 | Ohrui .................... | B01D 53/86 423/236 |
| 5,173,278 | A * | 12/1992 | Marler ............... | B01D 53/8621 208/113 |
| 5,316,991 | A | 5/1994 | Subramanian et al. | |
| 8,212,067 | B2 * | 7/2012 | Saitou ................... | C07C 253/34 558/463 |
| 2002/0143131 | A1 * | 10/2002 | Ward .................... | C07C 253/34 526/341 |
| 2004/0048210 | A1 * | 3/2004 | Monical ................. | B01D 53/56 431/4 |

FOREIGN PATENT DOCUMENTS

| | | | |
|---|---|---|---|
| CN | 101716462 A | 6/2010 | |
| CN | 102233231 A1 | 11/2011 | |
| DE | 2 488 870 A1 * | 4/1976 | ........... C07C 253/34 |

OTHER PUBLICATIONS

PCT Written Opinion for PCT Application No. PCT/CN2016/075602, 6 pgs. (dated Oct. 9, 2016).
Tetsuya Nanba, et al., "Active sites of Cu-ZSM-5 for the decomposition of acrylonitrile," Applied Catalysis B: Environmental, vol. 61, No. 3-4, pp. 288-296 (Jul. 20, 2005).
Notification of the First Office Action for Chinese Patent Application No. CN201610019224.6 with full English translation, dated May 16, 2017, 9 pages.
Notification of the Second Office Action for Chinese Patent Application No. CN201610019224.6 with full English translation, dated Aug. 10, 2017, 5 pages.
Notification to Grant Patent Right for Invention for Chinese Patent Application No. CN201610019224.6 with full English translation, dated Oct. 30, 2017, 2 pages.

* cited by examiner

INTEGRATED PURIFICATION METHOD AND SYSTEM FOR THE INDUSTRIAL EXHAUST GAS CONTAINING CYANIDES, HYDROCARBONS AND $NO_x$

CROSS-REFERENCE TO RELATED APPLICATIONS

This patent application is a U.S. National Phase Application under 35 U.S.C. § 371 of International Application No. PCT/CN2016/075602, filed on Mar. 4, 2016, entitled INTEGRATED PURIFICATION METHOD AND SYSTEM FOR THE INDUSTRIAL EXHAUST GAS CONTAINING CYANIDES, HYDROCARBONS AND NOx, which claims the benefit of priority of Chinese patent application no. 201610019224.6, filed Jan. 12, 2016.

TECHNICAL FIELD

The present invention relates to the field of exhaust gas purification, particularly relates to an integrated purification treatment process for treating the exhaust gas produced by acrylonitrile production device by the segmented selective catalytic combustion technology using a combination catalyst.

BACKGROUND ART

The exhaust gas discharged by the enterprises in the petrochemical industry and carbon fiber industry, such as acrylonitrile factory, synthetic rubber factory, plexiglass factory, carbon fiber factory, carbon factory and the like, is a highly toxic exhaust gas, which not only comprises hydrocarbons ($C_xH_y$), nitrogen oxides ($NO_x$), but also comprises the cyanide-containing substances (R—CN) such as acrylonitride, hydrocyanic acid and acetonitrile, the direct discharge thereof will inevitably cause serious environmental pollution problems.

The exhaust gas treatment in current chemical industry in China is usually performed by direct discharge or direct combustion, and it cannot guarantee the requirement of the sustainable development of the enterprise. However, the catalytic combustion technology has the advantages such as low ignition temperature, recoverable waste heat, low energy consumption, good selectivity and the like, it must be the mainstream of the purification technology for the exhaust gas containing cyanogens in the petrochemical industry and carbon fiber industry in future.

With respect to the acrylonitrile production device, it usually performs production by the propylene-oxidation process, and the final discharged exhaust gas usually contains cyanide-containing substances such as acrylonitrile, acetonitrile and HCN, meanwhile, since the raw material gas propylene is impurity, the exhaust gas usually accompanies with propane, ethane, unconverted propylene and other hydrocarbons, and it further comprises certain amount of environmentally harmful components such as nitrogen oxides, carbon monoxide and the like. Since the complexity, low concentration, high toxicity, and large gas flow of the combustible exothermic components in the exhaust gas, the general technology adopted cannot meet the environmental requirements.

With respect to the acrylonitrile exhaust gas treatment technology, there are mainly two processes of thermal incineration and catalytic oxidation at present. The thermal incineration process has the following disadvantages: it needs to supplement a large amount of fuel, its operating cost is high, the cyanide-containing (R—CN) substances tend to be converted to $N_x$ under high temperature, meanwhile the partial $N_2$ in the exhaust gas is oxidized to form $NO_x$ under high temperature, which tends to cause the secondary pollution and needs subsequent additional $NH_3$—SCR device to continue to remove, the requirements of the process parameters and removal effects are higher, and the process is more complex. However, when using catalytic oxidation process, under the action of the catalyst, the pollutants can be removed under the low temperature without supplementing additional fuel. Patent No. CN1903415 discloses that, the hydrocarbons in the exhaust gas from the acrylonitrile absorption tower are converted into carbon dioxide and water by using the catalytic oxidation process, but it does not account for the removal of $NO_x$ converted from R—CN by oxidation and $NO_x$ contained in the exhaust gas itself. Although the nitrogen in the exhaust gas will not continue to be converted to $NO_x$, its $NO_x$ emission is also excessive. Patent No. CN101362051A discloses an exhaust gas treatment process for acrylonitrile device, using an oxidation reactor in which the precious metal honeycomb is used as a catalyst and an $NH_3$—SCR reactor in which the vanadium/tungsten/titanium honeycomb ceramic is used as a catalyst, and the two reactors are combined to remove pollutants. The earlier stage reaction of the process is oxidation reaction, wherein the hydrocarbons, CO and R—CN are completely oxidized to produce $CO_2$, $H_2O$ and $NO_x$; and in the later stage, ammonia is used as the reducing agent to selective catalytic reduction of $NO_x$. The process not only needs two reactors simultaneously, which has a long process flow and large equipment investment in earlier stage, but also expends a large number of ammonia during operation, meanwhile, R—CN in earlier stage is converted into $NO_x$, which increases the load of the $NH_3$—SCR apparatus, has a risk of $NH_3$ leakage and overflow, and leads to excessive emissions of $NH_3$ which resulting in a new source of contamination. Therefore, the process still has room for improvement.

The supported precious metal catalyst has a strong oxidizing property and a excellent removal effect on hydrocarbons, but it does not have a selectivity to nitrogen formation to the removal of the cyanide-containing substances (R—CN), hence, when the discharge value of the cyanide-containing substances in exhaust gas is large, it is prone to cause excessive emission of $NO_x$ in exhaust gas. For the high content of hydrocarbons and large heat release of the reaction, the temperature of the catalyst bed is prone to higher than 550° C., and the nitrogenous substances are very prone to converted to $NO_x$ under this temperature, thus, the content of $NO_x$ in the exhaust gas is higher when the precious metal catalyst is used. It is understood that, after the exhaust gas from the acrylonitrile production passing through the precious metal catalyst bed, the concentration of $NO_x$ in the exhaust gas is sometimes up to 1000 mg/m³, and it must add a $NH_3$—SCR reactor subsequently for the removal of $NO_x$. The high concentration of $NO_x$ in the exhaust gas not only increases the consumption of $NH_3$, but also puts a higher requirement on the removal efficiency of SCR catalyst. Vanadium/tungsten/titanium catalysts also have the risk of harming the environment.

SUMMARY

The purpose of the present invention is to provide an integrated purification method for the industrial exhaust gas containing cyanides, hydrocarbons and nitrogen oxides to overcome the deficiencies in the prior art.

Another purpose of the present invention is to provide an integrated purification treatment system for the industrial exhaust gas containing cyanides, hydrocarbons and nitrogen oxides.

The technical solutions which can achieve the above-mentioned purposes of the present invention are as follows:

An integrated purification method for the industrial exhaust gas containing cyanides, hydrocarbons and nitrogen oxides, wherein the industrial exhaust gas is an industrial exhaust gas containing multi-component pollutants, comprising the steps of:

1) subjecting the exhaust gas containing pollutants such as cyanides, hydrocarbons and nitrogen oxides to a gas-liquid separation device to separate the free fluid, then mixing with the air blown by the air blower, and preheating by the heating unit;

2) entering into the selective catalytic combustion reactor (SCC reactor) for the selective catalytic combustion reaction, wherein the catalysis is performed in two stages in the SCC fixed bed reactor, the earlier stage is catalyzed by supported molecular sieve catalyst, and the latter stage is catalyzed by supported precious metal catalyst, the temperature of the inlet for entering into the SCC reactor is 280-350° C., the temperature of the catalyst in the earlier stage is controlled at 300-550° C., the temperature of the catalyst in the latter stage is controlled at 500-650° C., and the harmful substances are converted into $CO_2$, $H_2O$ and $N_2$ under the condition of a bed pressure of 0.5-25 kPa(G) (a pressure drop which can be tolerated by the bed); and 3) the gas came out from the SCC reactor entering into the heating unit to recover the heat, and then the purified exhaust gas being discharged directly through the chimney.

Furthermore, in the step 1), the total oxygen volume concentration in the exhaust gas before entering into the SCC reactor is controlled by the flow rate of the air supplemented by the air blower at 3% to 8%, preferably 5%.

Wherein, in the step 2), the temperature of the inlet of the SCC reactor is preferably 325° C., the temperature of the catalyst in the earlier stage bed is controlled at 430±20° C., and the temperature of the catalyst in the latter stage bed is controlled at 560±20° C.

Wherein, in the step 2), the supported molecular sieve catalyst in the earlier stage is a honeycomb monolithic catalyst or granular bundling catalyst, wherein the molecular sieve is one or more molecular sieves of ZSM-5 to ZSM-48 series, Beta, Y, MCM-22 to MCM-56 series, SAPO-5 to SAPO-47 series, SBA-15, SBA-16 and TS-1, the supported metal ion is one or more ions of copper, iron, cobalt, manganese, nickel, aluminum, silver and the like, preferably the honeycomb monolithic catalyst Cu-ZSM-5.

Wherein, in the step 2), a cordierite ceramic or a metal corrugated plate is used as the matrix in the precious metal catalyst in the latter stage, the precious metal is one or more of platinum, palladium, rhodium, silver and ruthenium, and the precious metal catalyst is preferably a platinum/palladium-cordierite honeycomb ceramic catalyst.

The supported molecular sieve catalyst, in particular the preferred Cu-ZSM-5 catalyst of the present invention, has a higher conversion rate of the removal of cyanide-containing substances and a higher selectivity to the nitrogen, and allows the R—CN to be converted to $N_2$, $CO_2$ and $H_2O$. In the temperature range of 350-500° C., the modified molecular sieve catalyst, in which propylene or propane is used as the reducing agent, can remove the $NO_x$ in the exhaust gas and convert it into nitrogen in high efficiency. Meanwhile, the bed temperature cannot be higher than 550° C., otherwise the higher the temperature, the more detrimental to the conversion of $NO_x$. However, most transition metal modified molecular sieve catalysts are difficult to achieve the complete removal of hydrocarbons, especially propane, ethane or methane, under the temperature of 550° C. or less, and it needs to rise to a higher temperature to meet the requirements. While the structure of the sieve catalyst is prone to change at a high temperature (above 600° C.), and the catalyst life is reduced. Meanwhile, the reactor is required to tolerate higher temperature.

Therefore, transition metal modified molecular sieves catalysts have the advantage of high nitrogen selectivity to the conversions of cyanide-containing substances and $NO_x$ at low temperatures, and precious metal catalysts have the advantage of efficient conversion of hydrocarbons. The integrated purification treatment process can be achieved by combing and optimizing two catalysts and controlling a suitable condition to display the both advantages.

Wherein, in the step 2), the ratio of the catalysts filling amounts in the earlier stage and the latter stage is in the range of 1-5:0-3, preferably 3:1.

An integrated purification treatment system for the industrial exhaust gas containing cyanides, hydrocarbons and $NO_x$, comprising a gas-liquid separation device, a heating unit and a SCC reactor (selective catalytic combustion reactor);

the gas-liquid separation device is provided with a gas outlet, a pipe connecting the gas outlet is connected to an exhaust gas inlet of the SCC reactor through the heating unit, the pipe connecting the gas outlet is provided with an air blower; an exhaust gas outlet of the SCC reactor is connected to a heating medium inlet of the heating unit through a pipe, and a heating medium outlet of the heating unit is connected with a chimney.

Wherein, the heating unit includes a heat recovery device and an electric heater, and the heat recovery device includes a steam heat exchanger, an exhaust heat boiler, and an exhaust gas heat exchanger.

Further, in the SCC reactor, a gas distributor, a molecular sieve honeycomb catalyst, an air re-distributor and a precious metal catalyst bed are sequentially provided in the direction from the exhaust gas inlet to the exhaust gas outlet.

Preferably, the purification treatment system for the exhaust gas includes two air blowers, wherein the outlet of the first air blower is connected to the pipe connecting to the gas outlet, the outlet of the second air blower is connected to the SCC reactor, and the inlet position is located between the molecular sieve honeycomb catalyst and the air re-distributor.

In the SCC reactor, the interior thereof is cooled by air to prevent the deactivation of catalyst caused by the excessive heat release and higher temperature.

The devices such as electric heater, steam superheater, exhaust heat boiler, exhaust gas heat exchanger, blower and the like are the standard devices.

The beneficial effects of the present invention are as follows:

The present invention can achieve the conversion of three pollutants containing cyanides (R—CN), hydrocarbons ($C_xH_y$) and nitrogen oxides ($NO_x$) simultaneously in the same reactor by reasonably installing the catalysts with different functions, without installing individual selective catalytic reduction denitration reactor and additional ammonia, and significantly simplifies the process. The present invention can achieve the exhaust gas treatment in multi-industry and multi-working conditions by adjusting the combination mode of the catalysts, and has wide application prospect.

BRIEF DESCRIPTION OF THE DRAWINGS

In the figures, 1 is the gas-liquid separation tank, 101 is the exhaust water pipe of the gas-liquid separation tank, 201 is the first air blower, 202 is the second air blower, 301 is the electric heater, 302 is the steam exchanger, 303 is the exhaust gas heat exchanger, 4 is the exhaust heat boiler, 401 is the water supply pipe of the boiler, 402 is the water vapor emptying device, 403 is the sewage pipe of the boiler, 5 is the SCC reactor, 501 is the exhaust gas inlet, 502 is the gas distributor, 503 is the molecular sieve honeycomb catalyst bed, 504 is the air re-distributor, 505 is the precious metal catalyst bed, 506 is the exhaust gas outlet, 6 is the chimney, and 7 is the air filter.

DETAILED DESCRIPTION

The present invention will be described through the following preferable examples. It will be understood by a person skilled in the art that the examples are only illustrative of the invention and are not intended to limit the scope of the present invention.

In the examples, unless otherwise specified, the used means are conventional means in the art.

The catalyst used in the examples is the catalyst developed by Beijing University of Chemical Technology. The main parameters of the catalyst are shown in Table 1.

TABLE 1

Main Parameters of the Catalyst

| | | Molecular sieve catalyst | Precious metal honeycomb ceramic catalyst |
|---|---|---|---|
| Type of the catalyst | | Honeycomb | Honeycomb |
| The main active ingredients | | Cu | Pt and Pd |
| The weight percentage content of the main active ingredients (wt %) | | 3~6 | Pt 0.13, Pd 0.05 |
| The components of the supporter | | ZSM-5 | Cordierite |
| Pore density | CPSI | 110 | 110 |
| Pitch-row | mm | 2.4 | 2.4 |
| Open area | % | 60 | 60 |
| Catalyst density | kg/m$^3$ | 670 | 490 |
| The sectional dimension of the catalyst block-length | mm | 75 | 150 |
| The sectional dimension of the catalyst block-wide | mm | 75 | 150 |
| The catalyst block-high | mm | 75 | 150 |

In Table 1, the catalyst block is the outer dimension of the honeycomb catalyst.

Example 1

The conditions of Examples 1 and 2 and Comparative Examples 1 and 2 were the simulation of the system constituted by the main gas in the exhaust gas of Example 3, and they are the experiments conducted in the laboratory with gas cylinders.

The experimental results of selective catalytic reduction of NO$_x$ by the molecular sieve catalysts at different oxygen concentrations were individually investigated in this Example, wherein propylene and propane were used as the reducing agents. The experimental conditions were: NO (200 mg/m$^3$)+C$_3$H$_6$ (2000 mg/m$^3$)+C$_3$H$_8$ (2000 mg/m$^3$)+CO (5000 mg/m$^3$), and the oxygen concentration was 5% (volume percentage, similarly hereinafter).

The molecular sieve honeycomb catalyst (Cu-ZSM-5) was used in the earlier stage, the honeycomb ceramic catalyst containing precious metal (the main components were platinum and palladium) was used in the latter stage, and the ratio of the filling amounts of the catalysts in the earlier stage and the latter stage was 3:1.

Example 2

The experimental conditions of Example 2 were: NO (200 mg/m$^3$)+C$_3$H$_6$ (2000 mg/m$^3$)+C$_3$H$_8$ (2000 mg/m$^3$)+CO (5000 mg/m$^3$), and the oxygen concentration was 8%.

Comparative Example 1 and Comparative Example 2

In Comparative Examples 1 and 2, the oxygen concentrations were 10% and 12%, respectively. Other experimental conditions were the same as that in Example 1, and the obtained results were shown in Table 2.

TABLE 2

Effects of different oxygen concentrations on the removal of NO$_x$ by molecular sieve catalysts

| Temperature (° C.) | Example 1 NO mg/m$^3$ | Example 2 NO mg/m$^3$ | Comparative Example 1 NO mg/m$^3$ | Comparative Example 2 NO mg/m$^3$ |
|---|---|---|---|---|
| 350 | 130 | 152 | 167 | 170 |
| 400 | 105 | 110 | 152 | 164 |
| 450 | 81 | 91 | 114 | 142 |
| 500 | 96 | 98 | 110 | 154 |
| 550 | 116 | 120 | 139 | 176 |

It can be seen from Examples 1 and 2 and Comparative Examples 1 and 2 that, in the molecular sieve catalyst bed, when the oxygen concentration is higher than 8%, the removal effect of NO$_x$ is poor. Meanwhile, when the temperature is higher than 500° C., the removal of NO$_x$ by the molecular sieve catalyst cannot reach the discharge standard. The higher oxygen concentration and higher temperature are not conducive to the removal of NO$_x$, it may be that propylene or propane cannot play the role of a reducing agent, and all of them were carried out the oxidation reaction. Therefore, the oxygen concentration of the exhaust gas must be controlled no higher than 8%, and the temperature of the molecular sieve catalyst bed cannot be higher than 550° C.

Therefore, the integrated purification treatment for the industrial exhaust gas containing multi-component pollutants such as cyanides, hydrocarbons and NO$_x$, can be achieved by the manner of combination catalysis and the reasonable design through precisely controlling the reaction conditions.

Example 3

Figure 1:
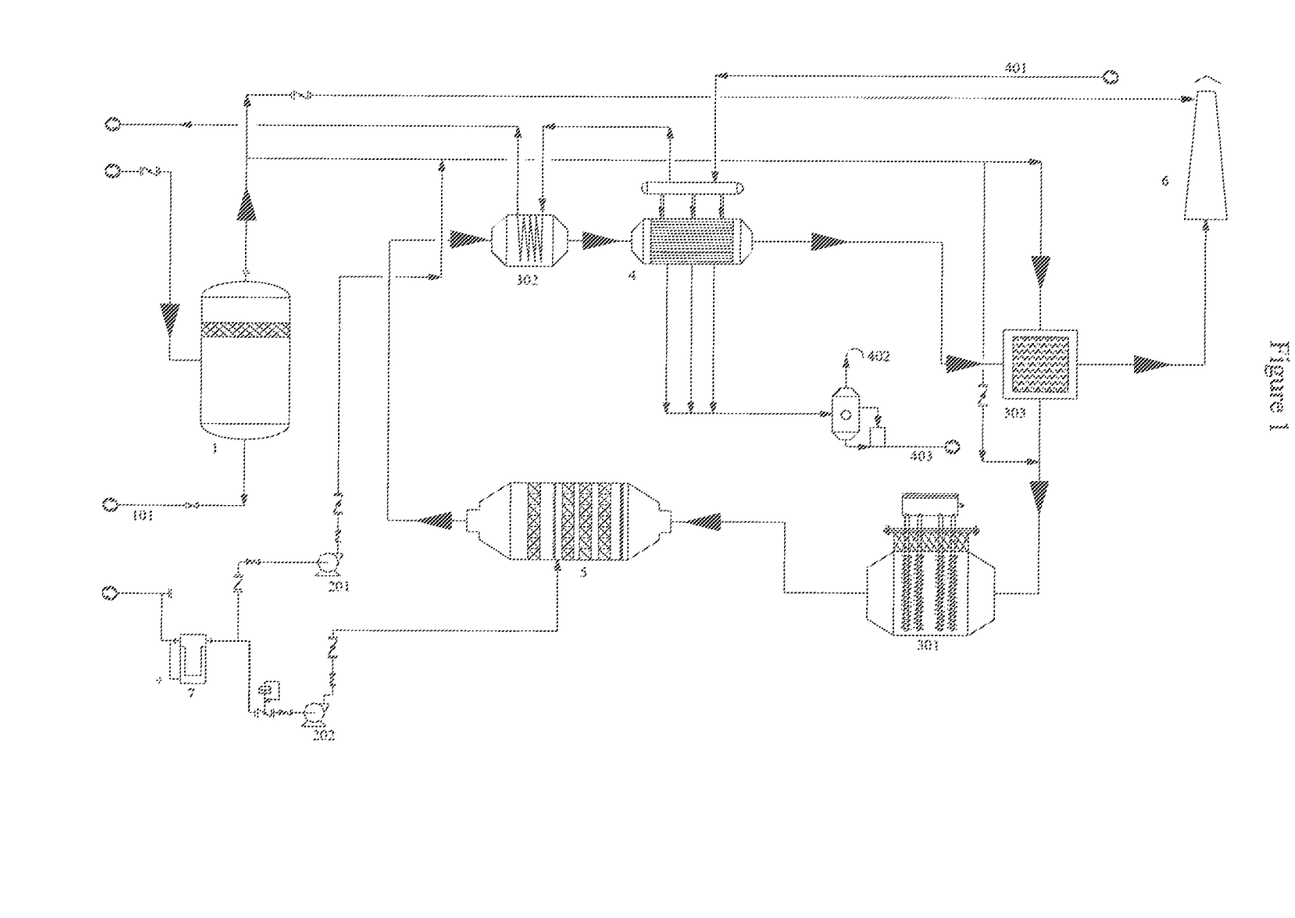
FIG. 1 is a process flow diagram of the integrated purification treatment process of the present invention.

Referring to FIG. 1, which showed an integrated purification treatment process for the exhaust gas produced by acrylonitrile production device, the used system includes a gas-liquid separation tank 1, a heating unit, and a SCC reactor 5.

The gas-liquid separation tank 1 was provided with a gas outlet, a pipe connecting the gas outlet was connected to an exhaust gas inlet of the SCC reactor through the heating unit, the pipe connecting the gas outlet was provided with an air blower; an exhaust gas outlet of the SCC reactor was connected to the heating medium inlet of the heating unit through a pipe, and a heating medium outlet of the heating unit was connected with a chimney.

Wherein, the heating unit included a heat recovery device and an electric heater 301, and the heat recovery device included a steam exchanger 302, an exhaust heat boiler 4, and an exhaust gas heat exchanger 303. The accessories of the exhaust heat boiler 4 included a water supply pipe of the boiler 401 connecting the pipe network, a sewage pipe of the boiler 403 discharged to the sewage system, and a water vapor emptying device 402.

Figure 2:
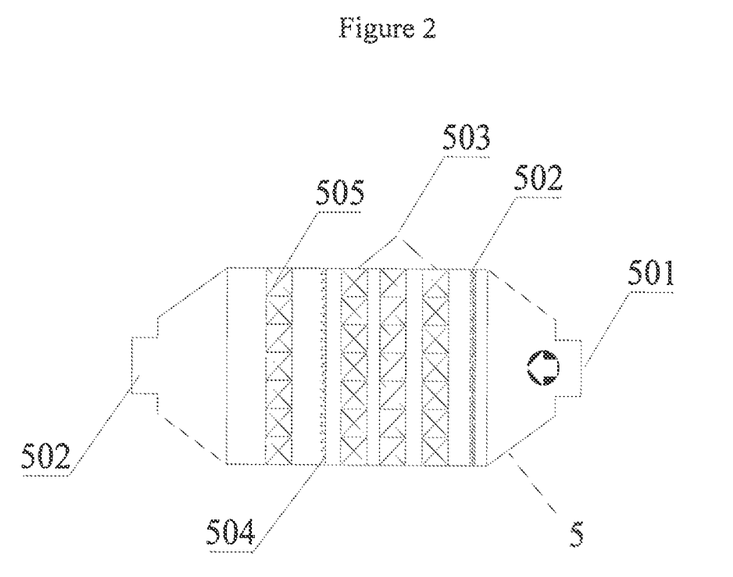
FIG. 2 is a schematic diagram of the internal structure of SCC reactor (5) of the present invention.

Referring to FIG. 2, in the SCC reactor 5, a gas distributor 502, a molecular sieve honeycomb catalyst bed 503, an air re-distributor 504, and a precious metal catalyst bed 505 were sequentially provided in the direction from the exhaust gas inlet 501 to the exhaust gas outlet 506.

The purification treatment system for the exhaust gas of the present Example included two air blowers, the air inlets thereof were connected to an air filter 7, the air inflow included air and nitrogen from the pipe network; wherein the outlet of the first air blower 201 was connected to the pipe connecting the gas outlet, the outlet of the second air blower was connected to the SCC reactor, and the inlet position was located between the molecular sieve honeycomb catalyst bed 503 and the air re-distributor 504.

The exhaust gas from the absorption tower of the acrylonitrile production separation device was subject to a gas-liquid separation tank 1 to separate the free fluid, and then mixed with air, and the air replenishment amount should be adjusted according to the controlled total oxygen concentration in exhaust gas (3% to 8%); after the preheating by the exhaust gas heat exchanger 303, wherein the electric heater in the process flow was used only at the driving mode, and was normally in the closed state, the pre heated exhaust gas enters the SCC reactor 5 for selective catalytic combustion reaction; in the fixed bed reactor, the catalyst bed was divided into two stages by the air re-distributor, the earlier stage was catalyzed by the supported molecular sieve honeycomb catalyst, and the later stage was catalyzed by the supported precious metal catalyst; the temperature of the inlet of the reactor was 280-350° C., the temperature of the catalyst in the earlier stage was 300-550° C., the temperature of the catalyst in the latter stage was 500-650° C. and the harmful substances were converted into $CO_2$, $H_2O$ and $N_2$ under the conditions of a bed pressure of 0.5-25 kPa(G) (a pressure drop which can be tolerated by the catalyst bed in the reactor). Wherein, the later bed temperature control was performed by appropriate replenishment by using blower according to the condition of the temperature rise of the reaction heat release. The purified gas from the SCC reactor was subject to the heat recovery devices such as steam superheater, exhaust heat boiler, and exhaust gas heat exchanger to recover heat, and then discharged directly through the chimney.

The specific processes and effects are reflected in the following tests.

Example 4

1) The exhaust gas containing pollutants such as cyanides, hydrocarbons and nitrogen oxides was firstly subjected to a gas-liquid separation device to separate the free fluid, then mixed with the air blown by the first air blower 201, and preheated by the heating unit;

2) after entering into the SCC reactor 5 for the selective catalytic combustion reaction, the catalysis was performed in two stages in the SCC fixed bed reactor R-101, the catalyst bed was divided into two stages by the air re-distributor 504 in the reactor, the earlier stage was catalyzed by the supported molecular sieve catalyst, and the latter stage was catalyzed by the supported precious metal catalyst, the temperature of the inlet for entering into the SCC reactor was 280° C., the temperature of the catalyst in the earlier stage was controlled at 338° C., the temperature of the catalyst in the latter stage was controlled at 518° C., and the harmful substances were converted into $CO_2$, $H_2O$ and $N_2$ under the condition of a bed pressure of 0.5-25 kPa(G); and 3) the gas came out from the SCC reactor 5 was subject to the heat recovery devices such as steam superheater 301, exhaust heat boiler 4, and exhaust gas heat exchanger 303 to recover heat, and the purified exhaust gas was discharged directly through the chimney 6.

The exhaust gases of Examples 4-9 and Comparative Examples 3-8 were derived from a company's 106,000 ton/year of acrylonitrile production device, the exhaust gas purification treatment system was the same as that of Example 3, and the working conditions were shown in Table 3:

TABLE 3

The components of the exhaust gas from a company's absorption tower

| Monitoring items | Numerical value |
| --- | --- |
| The total flow of the exhaust gas ($m^3$/h) | 50000~70000 |
| Acrylonitrile (mg/$Nm^3$) | 100~620 |
| Total non-methane hydrocarbon (mg/$m^3$) | 7000~12500 |
| Propane (mg/$m^3$) | 1000~3012 |
| Propylene (mg/$m^3$) | 1201~3059 |
| Ethane (mg/$m^3$) | 10~400 |
| Hydrocyanic acid (mg/$Nm^3$) | 0~60 |
| Acetonitrile (mg/$Nm^3$) | 0~50 |
| Nitrogen oxides(mg/$m^3$) | 200~435 |
| Oxygen concentration (%) | 1.1~7.2 |
| Nitrogen (%) | 89~91 |
| Temperature (° C.) | 35 |
| The pressure of the exhaust gas inlet kPa (G) | 20 |

Examples 5-9

In Example 4 to Example 9, a molecular sieve honeycomb catalyst (the main component was Cu-ZSM-5) was used in the earlier stage of the SCC reactor, a precious metal honeycomb ceramic catalyst (platinum/palladium-cordierite honeycomb ceramic catalyst) was used in the later stage, and the ratio of the catalysts filling amounts in the earlier stage and the latter stage was 3:1, the pressure in the reactor was about 5 kPa (G), and the removal effect of the exhaust gas was controlled by adjusting the temperatures of the inlet and the catalyst bed. The other process conditions were the same as those in Example 4, and the results were shown in Table 4.

TABLE 4

Test data obtained from Examples 4-9 and the national emission standard

| Items | Unit and name | Example 4 | Example 5 | Example 6 | Example 7 | Example 8 | Example 9 | National emission standard mg/m³ |
|---|---|---|---|---|---|---|---|---|
| Temperature | Inlet (° C.) | 280 | 325 | 347 | 327 | 338 | 327 | |
| | The temperature of the molecular sieve catalyst bed (° C.) | 338 | 432 | 451 | 488 | 469 | 454 | |
| | | 460 | 489 | 504 | 533 | 516 | 525 | |
| | The temperature of the precious metal catalyst bed (° C.) | 518 | 547 | 553 | 648 | 570 | 608 | |
| | Outlet (° C.) | 512 | 568 | 560 | 644 | 574 | 611 | |
| Outlet concentration (mg/m³) | Total non-methane hydrocarbon | 119 | 110 | 100 | 78 | 105 | 84 | 120 |
| | $NO_x$ | 77 | 89 | 94 | 99 | 84 | 93 | 100 |
| | Acrylonitrile | 2.6 | 5.2 | 5.6 | 3.6 | 5 | 4.5 | 22 |
| | Hydrocyanic acid | 1 | 1.2 | 0.5 | 0 | 0 | 0 | 1.9 |
| | Acetonitrile | 3 | 1 | 4.9 | 0 | 1.1 | 0 | none |

Comparative Examples 3-5

In Comparative Example 3 to Comparative Example 5, the molecular sieve honeycomb catalyst (the main component was Cu-ZSM-5) was used in the earlier and later stages of the SCC reactor, and the other process conditions were the same as those in Example 4, and the results were shown in Table 5.

TABLE 5

Test data obtained from the Comparative Example in which the molecular sieve catalyst was the only catalyst used and the national emission standard

| Items | Unit and name | Comparative Example 3 | Comparative Example 4 | Comparative Example 5 | National emission standard mg/m³ |
|---|---|---|---|---|---|
| Temperature | Inlet (° C.) | 295 | 325 | 345 | |
| | The bed temperature in the reactor in which the molecular sieve catalyst was only used (° C.) | 307 | 432 | 559 | |
| | | 378 | 489 | 609 | |
| | | 440 | 537 | 625 | |
| | Outlet (° C.) | 519 | 539 | 625 | |
| Outlet concentration (mg/m³) | Total non-methane hydrocarbon | 1210 | 756 | 109 | 120 |
| | $NO_x$ | 82 | 98 | 121 | 100 |
| | Acrylonitrile | 6.5 | 3.0 | 0.5 | 22 |
| | Hydrocyanic acid | 0.6 | 1.1 | 0 | 1.9 |
| | Acetonitrile | 1.1 | 2.4 | 0 | none |

In Comparative Examples 3 and 5, when the molecular sieve catalyst was the only catalyst used in the SCC reactor, the $NO_x$ can reach the national emission standard at low temperature, however, the $NO_x$ cannot reach the discharge standard when the temperature is higher than 600° C. With regard to hydrocarbons, it cannot reach the discharge standard at low temperature, while it can reach the discharge standard at high temperature. But the high temperature is not conducive to the removal of $NO_x$, and the catalyst cannot tolerate the high temperature of 600° C. or more for a long time.

Comparative Examples 6-8

In Comparative Example 6 to Comparative Example 8, the honeycomb ceramic catalyst containing precious metal (the main components were platinum and palladium) was used in the earlier and later stages of the SCC reactor, and the results were shown in Table 6.

TABLE 6

Test data obtained from the Comparative Examples in which the precious metal catalyst was the only catalyst used and the national emission standard

| Items | Unit and name | Comparative Example 6 | Comparative Example 7 | Comparative Example 8 | National emission standard mg/m³ |
|---|---|---|---|---|---|
| Temperature | Inlet (° C.) | 344 | 280 | 305 | |
| | The bed temperature in the reactor in which the precious metal catalyst was only used (° C.) | 575 | 520 | 539 | |
| | | 576 | 521 | 541 | |
| | | 571 | 525 | 545 | |
| | Outlet (° C.) | 576 | 524 | 561 | |
| Outlet concentration (mg/m³) | Total non-methane hydrocarbon | 81 | 102 | 99 | 120 |
| | $NO_x$ | 982 | 798 | 921 | 100 |
| | Acrylonitrile | 6.5 | 12.0 | 9.4 | 22 |
| | Hydrocyanic add | 0.6 | 1.1 | 0 | 1.9 |
| | Acetonitrile | 1.1 | 2.4 | 0 | none |

It can be seen from Examples 4 to 9 that, the substances containing cyanide, hydrocarbons and $NO_x$ can be removed and reach the national emission standard by the manner of combing the molecular sieve catalyst in the earlier stage and the precious metal catalyst in the latter stage and controlling the temperature in the SCC reactor.

The above results show that the integrated purification treatment for the industrial exhaust gas containing multi-component pollutants such as cyanides, hydrocarbons and $NO_x$ can be achieved by the manner of combination catalysis and reasonable design through precisely controlling the reaction conditions.

The embodiments described above are merely preferred embodiments of the present invention, but not intended to limit the scope of the invention. Those skilled in the art may make various modifications and improvements to the technical solutions of the present invention without departing from the designing spirit, which all fall within the protection scope defined by the appended claims of the invention.

INDUSTRIAL APPLICABILITY

The present invention provides an integrated purification method for the industrial exhaust gas of cyanides, hydrocarbons and $NO_x$, wherein the exhaust gas is an industrial exhaust gas containing multi-component pollutants. The method comprises the steps of: subjecting the exhaust gas containing pollutants such as cyanides, hydrocarbons and nitrogen oxides ($NO_x$) to a gas-liquid separation device to separate the free fluid, then mixing with the air blown by the air blower, and preheating by the heating unit; then entering into the SCC reactor for the selective catalytic combustion reaction, the gas came out from the SCC reactor entering into the heating unit to recover the heat, and then the purified exhaust gas being discharged directly through the chimney. The present invention can achieve the conversion of three pollutants containing cyanides (R—CN), hydrocarbons ($C_xH_y$) and nitrogen oxides ($NO_x$) simultaneously in the same reactor by reasonably installing the catalysts with different functions, without installing individual selective catalytic reduction denitration reactor and additional ammonia, and significantly simplifies the process. The present invention can achieve the exhaust gas treatment in multi-industry and multi-working conditions by adjusting the combination mode of the catalysts, and has wide application prospect.

What is claimed is:

1. An integrated purification method for an industrial exhaust gas of cyanides, hydrocarbons and $NO_x$, wherein the industrial exhaust gas is an industrial exhaust gas containing multi-component pollutants, comprising:
   1) subjecting the exhaust gas containing pollutants comprising cyanides, hydrocarbons and nitrogen oxides to a gas-liquid separation device to separate the free fluid, then mixing with the air blown by the air blower, and preheating by a heating unit;
   2) entering into a selective catalytic combustion reactor for the selective catalytic combustion reaction, wherein the catalysis is performed in two stages in the selective catalytic combustion reactor, the earlier stage is catalyzed by a supported molecular sieve catalyst, and the latter stage is catalyzed by a supported precious metal catalyst, the temperature of the inlet for entering into the selective catalytic combustion reactor is 280-350° C., the temperature of the catalyst in the earlier stage is controlled at 300-550° C., the temperature of the catalyst in the latter stage is controlled at 500-650° C., and the harmful substances are converted into $CO_2$, $H_2O$ and $N_2$ under the condition of a bed pressure of 0.5-25 kPa; and
   3) the gas emitted from the selective catalytic combustion reactor entering into the heating unit to recover the heat, and then the purified exhaust gas being discharged directly through a chimney.

2. The integrated purification method for the industrial exhaust gas according to claim 1, wherein in operation 1) the total oxygen volume concentration in the exhaust gas before entering into the SCC reactor is controlled by the flow rate of the air supplemented by the air blower at 3% to 8%.

3. The integrated purification method for the industrial exhaust gas according to claim 1, wherein in operation 2) the temperature of the inlet of the selective catalytic combustion reactor is 325° C., the temperature of the catalyst in the earlier stage bed is controlled at 430±20° C., and the temperature of the catalyst in the latter stage bed is controlled at 560±20° C.

4. The integrated purification method for the industrial exhaust gas according to claim 1, wherein in operation 2) the supported molecular sieve catalyst in the earlier stage is a honeycomb monolithic catalyst or granular bundling catalyst, wherein the molecular sieve is one or more molecular sieves selected from a group consisting of ZSM-5 to ZSM- 48 series, Beta, Y, MCM-22 to MCM-56 series, SAPO-5 to SAPO-47 series, SBA-15, SBA-16 and TS-1, the supported metal ion is one or more ions selected from a group consisting of copper, iron, cobalt, manganese, nickel, aluminum, and silver.

5. The integrated purification method for the industrial exhaust gas according to claim 1, wherein in operation 2) a cordierite ceramic or a metal corrugated plate is used as the matrix in the precious metal catalyst in the latter stage, the precious metal is one or more of platinum, palladium, rhodium, silver and ruthenium.

6. The integrated purification method for the industrial exhaust gas according to claim 1, wherein in operation 2) the ratio of the catalysts filling amounts in the earlier stage and the latter stage is in the range of 1-5:0-3.

7. An integrated purification treatment system for an industrial exhaust gas containing cyanides, hydrocarbons and $NO_x$, comprising:

a gas-liquid separation device, a heating unit and a selective catalytic combustion reactor, the gas-liquid separation device is provided with a gas outlet, a pipe connecting the gas outlet is connected to an exhaust gas inlet of the selective catalytic combustion reactor through the heating unit, the pipe connecting the gas outlet is provided with an air blower; an exhaust gas outlet of the selective catalytic combustion reactor is connected to a heating medium inlet of the heating unit through a pipe, and a heating medium outlet of the heating unit is connected with a chimney wherein the heating unit includes a heat recovery device and an electric heater, wherein the heat recovery device includes a steam exchanger, an exhaust heat boiler, and an exhaust gas heat exchanger.

8. The integrated purification treatment system for the industrial exhaust gas according to claim 7, wherein the selective catalytic combustion reactor, a gas distributor, a molecular sieve honeycomb catalyst, an air re-distributor and a precious metal catalyst bed are sequentially provided in the direction from the exhaust gas inlet to the exhaust gas outlet.

9. The integrated purification treatment system for the industrial exhaust gas according to claim 7, wherein the purification treatment system for the exhaust gas includes two air blowers, wherein the outlet of the first air blower is connected to the pipe connecting the gas outlet, the outlet of the second air blower is connected to the selective catalytic combustion reactor, and the inlet position is located between the molecular sieve honeycomb catalyst and the air re-distributor.

* * * * *